(12) United States Patent
Bardy et al.

(10) Patent No.: US 12,186,101 B2
(45) Date of Patent: Jan. 7, 2025

(54) INSERTABLE PHYSIOLOGICAL MONITOR INJECTOR TOOL

(71) Applicant: Bardy Diagnostics, Inc., Seattle, WA (US)

(72) Inventors: Gust H. Bardy, Carnation, WA (US); Jared Floyd, Ferndale, WA (US); John Choi, Seattle, WA (US); Daniel L. Reddy, Seattle, WA (US); Brian Cran, Seattle, WA (US)

(73) Assignee: Bardy Diagnostics, Inc., Seattle, WA (US)

(*) Notice: Subject to any disclaimer, the term of this patent is extended or adjusted under 35 U.S.C. 154(b) by 0 days.

(21) Appl. No.: 17/101,984

(22) Filed: Nov. 23, 2020

(65) Prior Publication Data
US 2021/0153813 A1 May 27, 2021

Related U.S. Application Data

(60) Provisional application No. 62/938,793, filed on Nov. 21, 2019.

(51) Int. Cl.
*A61B 5/00* (2006.01)

(52) U.S. Cl.
CPC .... *A61B 5/6865* (2013.01); *A61B 2560/0204* (2013.01); *A61B 2560/063* (2013.01)

(58) Field of Classification Search
CPC .......... A61B 5/6865; A61B 2560/0204; A61B 2560/063; A61B 2560/066; A61B 10/0233; A61B 10/04; A61B 2017/00353; A61B 17/32053; A61B 17/34; A61B 17/3415; A61B 17/3468; A61B 5/686; A61B 5/6846; A61B 17/1348; A61F 2/2436
(Continued)

(56) References Cited

U.S. PATENT DOCUMENTS

| | | | | | |
|---|---|---|---|---|---|
| 3,620,216 A | * | 11/1971 | Szymanski | ........... | A61M 37/00 604/60 |
| 4,223,674 A | * | 9/1980 | Fluent | ............... | A61M 37/0069 604/61 |

(Continued)

FOREIGN PATENT DOCUMENTS

| WO | WO 03/065926 A2 | 8/2003 |
|---|---|---|
| WO | WO 2008/005015 A1 | 1/2008 |

(Continued)

OTHER PUBLICATIONS

May 2, 2022 Letter From Counsel. 1:22-cv-00351-CFC. May 2, 2022.

(Continued)

*Primary Examiner* — Jacqueline Cheng
*Assistant Examiner* — Tho Q Tran
(74) *Attorney, Agent, or Firm* — K&L Gates LLP

(57) ABSTRACT

An insertable physiological monitor injector tool is provided. An elongated handle includes a recess formed along a longitudinal axis and has an opening on a distal end. An insertion tube has a hollow elongated shape that is movably positioned within the elongated handle, in the recess. A stationary arbor is affixed on a proximal end to a proximal end of the elongated handle and extends through the insertion tube when the insertion tube is in a retracted position. A tab is affixed to the insertion tube, wherein the tab can lock the insertion tube in an extended position.

16 Claims, 11 Drawing Sheets

(58) Field of Classification Search
USPC .......................................................... 604/502
See application file for complete search history.

(56) References Cited

U.S. PATENT DOCUMENTS

| | | | |
|---|---|---|---|
| 4,846,793 A * | 7/1989 | Leonard ............ | A61M 37/0069 604/60 |
| 5,176,649 A * | 1/1993 | Wakabayashi .... | A61M 39/0247 604/164.09 |
| 5,281,197 A * | 1/1994 | Arias ................ | A61M 37/0069 604/209 |
| 5,862,803 A | 1/1999 | Besson et al. | |
| 6,190,350 B1 * | 2/2001 | Davis ....................... | A61J 1/00 604/61 |
| 6,248,112 B1 * | 6/2001 | Gambale ............ | A61B 17/3468 606/108 |
| 7,197,357 B2 | 3/2007 | Istvan et al. | |
| 7,206,630 B1 | 4/2007 | Tarler | |
| 7,212,849 B2 | 5/2007 | Zhang et al. | |
| 7,395,106 B2 | 7/2008 | Ryu et al. | |
| 7,468,032 B2 | 12/2008 | Stahmann et al. | |
| 7,736,330 B2 | 6/2010 | Bardy | |
| 8,150,502 B2 | 4/2012 | Kumar et al. | |
| 8,214,007 B2 | 7/2012 | Baker et al. | |
| 8,315,695 B2 | 11/2012 | Sebelius et al. | |
| 8,483,809 B2 | 7/2013 | Kim et al. | |
| 8,538,503 B2 | 9/2013 | Kumar et al. | |
| 8,611,980 B2 | 12/2013 | Choe et al. | |
| 8,647,268 B2 | 2/2014 | Tran | |
| 8,718,742 B2 | 5/2014 | Beck et al. | |
| 8,926,509 B2 | 1/2015 | Magar et al. | |
| 9,211,073 B2 | 12/2015 | Banet et al. | |
| 9,277,864 B2 | 3/2016 | Yang et al. | |
| 9,510,755 B2 | 12/2016 | Fong et al. | |
| 9,597,143 B2 * | 3/2017 | Madan .................... | H02J 50/80 |
| 9,669,212 B2 | 6/2017 | Mueller et al. | |
| 10,327,660 B2 | 6/2019 | Gallego et al. | |
| 10,413,251 B2 | 9/2019 | Golda et al. | |
| 10,441,185 B2 | 10/2019 | Rogers et al. | |
| 10,548,632 B2 * | 2/2020 | Sick ................ | A61B 17/32093 |
| 11,051,743 B2 | 7/2021 | Felix et al. | |
| 11,116,447 B2 | 9/2021 | Yang et al. | |
| 11,445,967 B2 | 9/2022 | Felix et al. | |
| 2004/0111095 A1 * | 6/2004 | Gordon ..................... | A61F 2/95 606/108 |
| 2004/0199140 A1 * | 10/2004 | Rue ................... | A61M 37/0069 604/506 |
| 2007/0249992 A1 * | 10/2007 | Bardy ............... | A61M 37/0069 604/60 |
| 2008/0091089 A1 | 4/2008 | Guillory et al. | |
| 2009/0062670 A1 | 3/2009 | Sterling et al. | |
| 2009/0099469 A1 | 4/2009 | Flores | |
| 2009/0177073 A1 | 7/2009 | Sonnenborg | |
| 2009/0182204 A1 | 7/2009 | Semler et al. | |
| 2010/0022863 A1 * | 1/2010 | Mogensen ....... | A61B 5/150412 600/365 |
| 2011/0009729 A1 | 1/2011 | Shin et al. | |
| 2011/0041613 A1 * | 2/2011 | Tran ....................... | A61N 1/372 73/632 |
| 2011/0054285 A1 | 3/2011 | Searle et al. | |
| 2011/0077497 A1 | 3/2011 | Oster et al. | |
| 2011/0125040 A1 | 5/2011 | Crawford et al. | |
| 2012/0323098 A1 | 12/2012 | Moein et al. | |
| 2013/0225967 A1 | 8/2013 | Esposito | |
| 2014/0276928 A1 | 9/2014 | Vanderpool et al. | |
| 2014/0324067 A1 | 10/2014 | Emken et al. | |
| 2015/0022372 A1 | 1/2015 | Vosch | |
| 2015/0032062 A1 * | 1/2015 | Jakob ................. | A61M 5/3202 604/198 |
| 2015/0087950 A1 | 3/2015 | Felix et al. | |
| 2016/0066850 A1 * | 3/2016 | Brockway .............. | A61B 5/076 600/302 |
| 2016/0235346 A1 | 8/2016 | Liu et al. | |
| 2018/0168686 A1 | 6/2018 | Jin et al. | |
| 2018/0256108 A1 * | 9/2018 | Au-Yeung .......... | A61B 17/3468 |
| 2018/0280056 A1 | 10/2018 | Austin et al. | |
| 2019/0223806 A1 | 7/2019 | Bennet et al. | |

FOREIGN PATENT DOCUMENTS

| | | |
|---|---|---|
| WO | 2010104952 | 9/2010 |
| WO | WO 2010/104952 A2 | 9/2010 |
| WO | WO2012015955 * | 2/2012 |

OTHER PUBLICATIONS

May 24, 2022 Letter to Opposing Counsel. 1:22-cv-00351-CFC. May 24, 2022.

Complaint from Case No. 1:22-cv-00351-UNA, *Bardy Diagnostics, Inc.* (Plaintiff) v. *Vital Connect, Inc.* (Defendant), Filed: Mar. 18, 2022, 182 pages.

Defendant's Opening Brief In Support of Its Motion To Dismiss For Failure to State A Claim from Case No. 1:22-cv-00351-CFC, *Bardy Diagnostics, Inc.* (Plaintiff) v. *Vital Connect, Inc.* (Defendant), Filed: May 25, 2022, 18 pages.

Defendant's Answer, Defenses, and Counterclaim from Case No. 1:22-cv-00351-CFC, *Bardy Diagnostics, Inc.* (Plaintiff) v. *Vital Connect, Inc.* (Defendant), Filed: May 25, 2022, 132 pages.

Plaintiff's Answering Brief In Opposition to Defendant's Motion to Dismiss For Failure to State a Claim from Case No. 1:22-cv-00351-CFC, *Bardy Diagnostics, Inc.* (Plaintiff) v. *Vital Connect, Inc.* (Defendant), Filed: Jun. 8, 2022, 25 pages.

Plaintiff's Answer to Defendant's Counterclaim from Case No. 1:22-cv-00351-CFC, *Bardy Diagnostics, Inc.* (Plaintiff) v. *Vital Connect, Inc.* (Defendant), Filed: Jun. 15, 2022, 5 pages.

Defendant's Reply Brief In Support of Its Motion to Dismiss For Failure to State a Claim from Case No. 1:22-cv-00351- CFC, *Bardy Diagnostics, Inc.* (Plaintiff) v. *Vital Connect, Inc.* (Defendant), Filed: Jun. 15, 2022, 93 pages.

Oct. 17, 2022 Letter to Opposing Counsel, *Bardy Diagnostics, Inc.* (Plaintiff) v. *Vital Connect, Inc.*, No. 22-cv-00351-CFC (D. Del.), Oct. 17, 2022.

Nov. 11, 2022, Letter from Opposing Counsel, 1:22-cv-00351-CJB; *Bardy Diagnostics, Inc.* (Plaintiff) v. *Vital Connect, Inc.* (D. Del.), Nov. 11, 2022.

Dec. 26, 2022 Letter from Opposing Counsel, 1:22-cv-00351-CJB; *Bardy Diagnostics, Inc.* (Plaintiff) v. *Vital Connect, Inc.* (D. Del.); and IPR2023-00381; *Vital Connect, Inc.* v. *Bardy Diagnostics, Inc.* (P.T.A.B.), Dec. 26, 2022.

First Amended Complaint for Patent Infringement, 1:22-cv-00351-CJB, *Bardy Diagnostics, Inc.* (Plaintiff) v. *Vital Connect, Inc.* (D. Del.), filed Jan. 10, 2023.

Petition for Inter Partes Review of U.S. Pat. No. 11,051,743 Pursuant To 35 U.S.C. §§ 311-319 and 37 C.F.R. § 42, Case No. IPR2023-00381, *Vital Connect, Inc.* v. *Bardy Diagnostics, Inc.* (P.T.A.B.), Dec. 21, 2022, 875 pages.

Defendant's Answer to First Amended Complaint, Defenses, and Counterclaim, 1:22-cv-00351-CJB, *Bardy Diagnostics, Inc.* v. *Vital Connect, Inc.* (D. Del.), filed Jan. 24, 2023 (227 pages).

[Corrected] Chart CC-2 Invalidity Contentions: U.S. Pat. No. 11,445,967; Case No. 22-351-CJB (Delaware); Invalidity of U.S. Patent No. by U.S. Pat. Pub. No. 2011/0077497 ("Oster") and U.S. Pat. No. 11,116,447 ("Yang"); Oct. 25, 2023; 16 pages.

[Corrected] Chart C-2 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster") and U.S. Pat. No. 11,116,447 ("Yang"); Oct. 25, 2023; 22 pages.

Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar") and U.S. Pat. No. 11,116,447 ("Yang"); Oct. 25, 2023; 24 pages.

Chart C-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar") and U.S. Pat. No. 11,116,447 ("Yang"); Oct. 25, 2023; 32 pages.

(56) References Cited

OTHER PUBLICATIONS

Chart B-7 Invalidity Contentions: U.S. Pat. No. 11,051,743 and U.S. Pat. No. 11,445,967; Case No. 22-351-CJB (Delaware); A Patch Comprising Adhered Layers; Oct. 25, 2023; 16 pages.
Chart B-6 Invalidity Contentions: U.S. Pat. No. 11,051,743 and U.S. Pat. No. 11,445,967; Case No. 22-351-CJB (Delaware); Hydrocolloid Adhesives on a Portion of the Backing; Oct. 25, 2023; 5 pages.
Chart B-5 Invalidity Contentions: U.S. Pat. No. 11,051,743 and U.S. Pat. No. 11,445,967; Case No. 22-351-CJB (Delaware); Conversion of Electrocardiogramals From One Format to Another; Oct. 25, 2023; 6 pages.
Chart B-4 Invalidity Contentions: U.S. Pat. No. 11,051,743 and U.S. Pat. No. 11,445,967; The Case No. 22-351-CJB (Delaware); Rounded Outer Edge of Backing Ends; Oct. 25, 2023; 5 pages.
Chart B-3 Invalidity Contentions: U.S. Pat. No. 11,051,743 and U.S. Pat. No. 11,445,967; Case No. 22-351-CJB (Delaware); Flexible Circuit Comprising a Pair of Circuit Traces To Couple Electrodes; Oct. 25, 2023; 8 pages.
Chart B-2 Invalidity Contentions: U.S. Pat. No. 11,051,743 and U.S. Pat. No. 11,445,967; Case No. 22-351-CJB (Delaware); An Electrocardiogramactrode On Each End Of The Backing; Oct. 25, 2023; 8 pages.
Chart B-1 Invalidity Contentions: U.S. Pat. No. 11,051,743 and U.S. Pat. No. 11,445,967; Case No. 22-351-CJB (Delaware); Elongated Strip With Narrowed Midsection; Oct. 25, 2023; 8 pages.
Chart AA-10 Invalidity Contentions: U.S. Pat. No. 11,445,967; Case No. 22-351-CJB (Delaware); Invalidity of U.S. Pat. No. 11,445,967 by WO 2003/065926 ("Ozguz"); Oct. 25, 2023; 6 pages.
Chart AA-9 Invalidity Contentions: U.S. Pat. No. 11,445,967; Case No. 22-351-CJB (Delaware); Invalidity of U.S. Pat. No. 11,445,967 by U.S. Pat. Pub. No. 2011/0009729 ("Shin"); Oct. 25, 2023; 6 pages.
Chart AA-8 Invalidity Contentions: U.S. Pat. No. 11,445,967; Case No. 22-351-CJB (Delaware); Invalidity of U.S. Pat. No. 11,445,967 by WO 2008/005015 ("Shennib"); Oct. 25, 2023; 6 pages.
Chart AA-7 Invalidity Contentions: U.S. Pat. No. 11,445,967; Case No. 22-351-CJB (Delaware); Invalidity of U.S. Pat. No. 11,445,967 by U.S. Pat. No. 7,206,630 ("Tarler"); Oct. 25, 2023; 7 pages.
Chart AA-6 Invalidity Contentions: U.S. Pat. No. 11,445,967; Case No. 22-351-CJB (Delaware); Invalidity of U.S. Pat. No. 11,445,967 by U.S. Pat. No. 9,669,212 ("Mueller"); Oct. 25, 2023; 6 pages.
Chart AA-5 Invalidity Contentions: U.S. Pat. No. 11,445,967; Case No. 22-351-CJB (Delaware); Invalidity of U.S. Pat. No. 11,445,967 by U.S. Pat. No. 10,413,251 ("Golda"); Oct. 25, 2023; 6 pages.
Chart A-4 Invalidity Contentions: U.S. Pat. No. 11,445,967; Case No. 22-351-CJB (Delaware); Invalidity of U.S. Pat. No. 11,445,967 by U.S. Pat. Pub. No. 2011/0077497 ("Oster"); Oct. 25, 2023; 6 pages.
Chart A-3 Invalidity Contentions: U.S. Pat. No. 11,445,967; Case No. 22-351-CJB (Delaware); Invalidity of U.S. Pat. No. 11,445,967 by U.S. Pat. No. 10,327,660 ("Gallego"); Oct. 25, 2023; 7 pages.
Chart AA-2 Invalidity Contentions: U.S. Pat. No. 11,445,967; Case No. 22-351-CJB (Delaware); Invalidity of U.S. Pat. No. 11,445,967 by U.S. Pat. No. 11,116,447 ("Yang"); Oct. 25, 2023; 14 pages.
Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar"); Oct. 25, 2023; 13 pages.
Chart A-10 Invalidity Contentions: U.S. Pat. No. 11,051,743; Case No. 22-351-CJB (Delaware); Invalidity of U.S. Pat. No. 11,051,743 by WO 2003/065926 ("Ozguz"); Oct. 25, 2023; 12 pages.
Chart A-9 Invalidity Contentions: U.S. Pat. No. 11,051,743; Case No. 22-351-CJB (Delaware); Invalidity of U.S. Pat. No. 11,051,743 by U.S. Pat. Pub. No. 2011/0009729 ("Shin"); Oct. 25, 2023; 12 pages.
Chart A-8 Invalidity Contentions: U.S. Pat. No. 11,051,743; Case No. 22-351-CJB (Delaware); Invalidity of U.S. Pat. No. 11,051,743 by WO 2008/005015 ("Shennib"); Oct. 25, 2023; 12 pages.
Chart A-7 Invalidity Contentions: U.S. Pat. No. 11,051,743; Case No. 22-351-CJB (Delaware); Invalidity of U.S. Pat. No. 11,051,743 by U.S. Pat. No. 7,206,630 ("Tarler"); Oct. 25, 2023; 12 pages.
Chart A-6 Invalidity Contentions: U.S. Pat. No. 11,051,743; Case No. 22-351-CJB (Delaware); Invalidity of U.S. Pat. No. 11,051,743 by U.S. Pat. No. 9,669,212 ("Mueller"); Oct. 25, 2023; 11 pages.
Chart A-5 Invalidity Contentions: U.S. Pat. No. 11,051,743; Case No. 22-351-CJB (Delaware); Invalidity of U.S. Pat. No. 11,051,743 by U.S. Pat. No. 10,413,251 ("Golda"); Oct. 25, 2023; 11 pages.
Chart A-4 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster"); Oct. 25, 2023; 11 pages.
Chart A-3 Invalidity Contentions: U.S. Pat. No. 11,051,743; Case No. 22-351-CJB (Delaware); Invalidity of U.S. Pat. No. 11,051,743 by U.S. Pat. No. 10,327,660 ("Gallego"); Oct. 25, 2023; 12 pages.
Chart A-2 Invalidity Contentions: U.S. Pat. No. 11,051,743; Case No. 22-351-CJB (Delaware); Invalidity of U.S. Pat. No. 11,051,743 by U.S. Pat. No. 11,116,447 ("Yang"); Oct. 25, 2023; 19 pages.
Chart A-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar"); Oct. 25, 2023; 19 pages.
*Bardy Diagnostics, Inc.*, Plaintiff v. *Vital Connect, Inc.*; The United States District Court for the District of Delaware; C.A. No. 22-351 (CJB); Vitalconnect's Preliminary Invalidity Contentions; filed Oct. 25, 2023.
Wolf, "The Data-Driven Life," New York Times Magazine, Apr. 28, 2010, 13 pages.
Hill, "Adventures in Self-Surveillance: Fitbit, Tracking My Movement and Sleep," Forbes, Feb. 25, 2011, 11 pages.
Mehen, "Open health with the quantified self," Opensource.com, Aug. 25, 2011, 7 pages.
"23 Personal Tools to Learn More About Yourself," Flowingdata.com, Sep. 18, 2008, 18 pages.
Puurtinen et al., "Estimation of ECG Signal of closely separated bipolar electrodes using thorax models," Proceedings of the 26th Annual International Conference of the IEEE EMBS pp. 801-804, San Francisco, Calif., USA, Sep. 1-5, 2004, 4 pages.
TrägÅrdh et al., How many ECG leads do we need? Cardiol Clin. Aug. 2006;24(3):317-30, vii. doi: 10.1016/j.ccl.2006.04.005. PMID: 16939826; 14 pages.
Adams et al., U.S. Appl. No. 61/755,623, filed Jan. 23, 2013, 48 pages.
Toth et al., U.S. Appl. No. 61/832,131, filed Jun. 6, 2013, 82 pages.
Vishnubhotla, "Pre-processing of ECG signals for ambulatory use," Jan. 2009; 5 pages.
Chaimanonart et al., "A wireless batteryless in vivo EKG and body temperature sensing microsystem with adaptive RF powering for genetically engineered mice monitoring," Jul. 2009; 4 pages.
Alzaidi et al., "Smart Textiles Based Wireless ECG System," May 2012; 5 pages.
Saeed et al., "A Scalable Wireless Body Area Sensor Network for Health-Care Monitoring," Jun. 2009, 4 pages.
Pandian et al., "Wireless Sensor Network for Wearable Physiological Monitoring," Journal of Networks, vol. 3, No. 5, May 2008; 15 pages.
Mukala et al., "A Novel Zigbee-based Low-cost, Low-Power Wireless EKG system," IEEE, May 2010; 4 pages.
Aventyn, Inc., "Vital Connect, Aventyn Launch Wearable Biosensor Platform for Mobile Patient Monitoring", Dec. 12, 2013, 5 pages.
Anand et al., "Design of the Multi-Sensor Monitoring in Congestive Heart Failure (MUSIC) Study: Prospective Trial to Assess the Utility of Continuous Wireless Physiologic Monitoring in Heart Failure", Journal of Cardiac Failure, vol. 17, No. 1, Jan. 1, 2011, pp. 11-16 (6 pages).
Cesario et al., "Arrhythmia Detection with a Low-Profile Wireless Adherent Cardiac Monitor: Results from the ADAM and EVE Studies", The Journal of Innovations in Cardiac Rhythm Management, 2 (2011) Sep. 2011, pp. 476-482, (7 pages).

(56) References Cited

OTHER PUBLICATIONS

Corventis Nuvant, "Nuvant Mobile Cardiac Telementry (MTC) System", Corventis, 2009, last printed Jul. 18, 2024, https://web.archive.org/web/20100127193736/http://corventis.com/AP/nuvant.asp.

Corventis Avivo, "Avivo Mobile Patient Management System", Corventis, 2008, lasted printed Jul. 18, 2024, https://web.archive.org/web/20100118155329/http://www.corventis.com/AP/avivo.asp.

IRhythm ZIO XT Patch/Event Card, "Zio Patch", iRhythm, 2011, last printed Jul. 18, 2024, https://web.archive.org/web/20111017074139/http://irhythmtech.com/media/files/Z100A4020.04%20-%20ZIO%20PATCH%20DATA%20SHEET.pdf.

*Bardy Diagnostics, Inc.* v. *Vital Connect, Inc.*, Defendant's Identification of Supplemental Prior Art References, C.A. No. 22-351 (CJV), May 22, 2024.

International Preliminary Report on Patentability and Written Opinion, PCT/US2019/064331, Jun. 8, 2021.

First Examination Report, Communication pursuant to Article 94(3) EPC, 19 828 053.9-1113, dated Apr. 15, 2024.

* cited by examiner

20

45

50

65

120

INSERTABLE PHYSIOLOGICAL MONITOR INJECTOR TOOL

CROSS-REFERENCE TO RELATED APPLICATION

This non-provisional patent application claims priority under 35 U.S.C. § 119(e) to U.S. Provisional Patent Application, Ser. No. 62/938,793, filed Nov. 21, 2019, the disclosures of which are incorporated by reference.

FIELD

This application relates in general to medical tools, and in particular to an insertable physiological monitor injector tool.

BACKGROUND

Medical diagnosis includes evaluating patient physiology, which describes the vital functions of the patient's anatomical structure, that is, the living body and its organs. A patient's physiology is determined through medical diagnostic procedures that include performing medical tests and, when available, reviewing patient data that has been collected through monitoring, although the data should first be correlated to patient symptoms to be of relevant diagnostic value.

Sporadic conditions present a special challenge because diagnostic tests performed in a physician's office may prove ineffective if the sporadic condition fails to present while the test is being performed. Sporadic conditions may be due to chronic or acute cause and can include transient signs, such as erratic heartbeat, muscle or nerve spasms, or hypoglycemia (or hyperglycemia) that may be accompanied by discernable symptoms. The unpredictable nature of sporadic conditions often makes the capturing of physiological data a matter of good timing. If the sporadic condition fails to occur during the course of a medical test, no physiological data, and therefore no diagnostic insight, is obtained.

In response, physicians have turned to ambulatory monitoring, which utilizes sensors placed cutaneously on or implanted within a patient's body that are attached to a recorder to provide physiological data capture while the patient goes about daily life.

Ambulatory monitors that are either wholly implanted inside the patient's body or which use implanted sensors will generally provide cleaner physiological data relatively free of environmental noise and effects, especially when compared to data captured cutaneously. However, a tool or other means for performing implantation of the ambulatory monitor is required. Implantation can be invasive to some degree and carries more risk than cutaneous or external forms of ambulatory monitoring. Accordingly, such implantation means must be minimally invasive and ensure low risk of harm to a wearer of the monitor.

Current implantation tools include a tool described in U.S. Patent Application Publication No. 2018/0280056, to Austin, which includes a core having a longitudinal recess and a shell that protrudes from an end of the core that forms a compartment for a medical implant. A rod is arranged in the longitudinal recess and is connected to a grip member that encompasses the core. After the shell has been inserted into a patient, a user holds the grip member and the core retracts by sliding within the grip member to slide the rod for keeping position of the medical implant at the implantation side as the core retracts. Withdrawal of the core and shell from a patient depends on the user that pulls the core out of the incision site, which can create risk to a patient, such as if the user pulls the device out too fast or at an incorrect angle, potentially causing a larger incision to form or tissue damage.

Another implantation tool is described by U.S. Patent Application, Publication No. 2018/0168686, to Jin that includes an insertion housing having a passage and an obturator with a receptacle that is in communication with the passage of the housing. A distal end of the obturator is inserted through an incision on a patient and force is applied to the obturator to maintain the distal end within the patient as extended from the insertion housing. When in place, the obturator is withdrawn, allowing an implant to drop into the passage and the obturator is then moved forcing the implant to discharge from the tool. Thus, implant requires multiple steps for movement of the obturator, including withdrawing the obturator from an extended position, movement of the obturator back to the extended position to force the implant into the patient. Both injector tools referenced above are used for non-rechargeable battery powered devices and thus, fail to provide a means for recharging if the implant is packaged with the injector tool.

Therefore, a need remains for an implant tool that safely and quickly injects a medical implant in a patient, while lowering risk of injury to the patient in a least invasive way, as well as simultaneously allowing for rechargeability of the medical implant that sits in the injector tool awaiting delivery to the patient. Devices may require recharging after packaging as they await implant into a patient, sometimes over months-long periods of time. Consequently, devices with rechargeable battery systems must use an injector technology that allows for recharging in situ. Accordingly, this injector accomplishes both safer insertion but also rechargeability while in the injector.

SUMMARY

An insertable physiological monitor injector tool includes a handle within which an arbor and insertion tube are positioned. The insertion tube can have a hollow cylindrical form and be sized to house the arbor. A button can be positioned on an outer surface of the handle to retract the insertion tube when pressed or pulled back. During retraction of the insertion tube, the arbor remains stationary. The insertion tube is extended and preloaded with an insertable physiological monitor (IPM), such that one end of the IPM is adjacent to a distal end of the arbor. Examples of the IPM can include monitors for cardiac, oxygen, blood pressure, and glucose, as well as other types of monitors.

The insertion tube is inserted into the skin of a patient, at an angle, and the injector tool is rotated to lay flat along the skin to lift the skin up while performing a tunneling action. Once the insertion tube has reached a desired location for the IPM, the button is pressed to retract the insertion tube. The stationary arbor ensures the IPM remains in place, in the patient by preventing movement of the IPM with the insertion tube as the insertion tube retracts. Subsequently, injector tool is removed from the patient.

An embodiment provides an insertable physiological monitor injector tool. An elongated handle includes a recess formed along a longitudinal axis and has an opening on a distal end. An insertion tube has a hollow elongated shape that is movably positioned within the elongated handle, in the recess. A stationary arbor is affixed on a proximal end to a proximal end of the elongated handle and extends through the insertion tube when the insertion tube is in a retracted position. A tab is affixed to the insertion tube, wherein the tab can lock the insertion tube in an extended position.

A further embodiment provides an insertable physiological monitor injector tool having a structure through which a monitor housed in the structure is rechargeable.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, including time and clustering of events, all without departing from their spirit and the scope. Accordingly, the drawings and detailed description are to be regarded as illustrative in nature and not as restrictive.

DETAILED DESCRIPTION

Implantable devices can provide patients with benefits, such as continuous monitoring of physiological signals, which can be helpful to detect sporadic events and facilitate diagnosis by a medical professional. However, injecting the implantable device can be invasive and come with some risk to the patient, such as infection or adverse reaction due to penetrating the patient's skin during injection. An injection tool that is minimally invasive, such as requiring a small incision, and is quick and efficient for implantation can help reduce risk to the patient.

Figure 1:
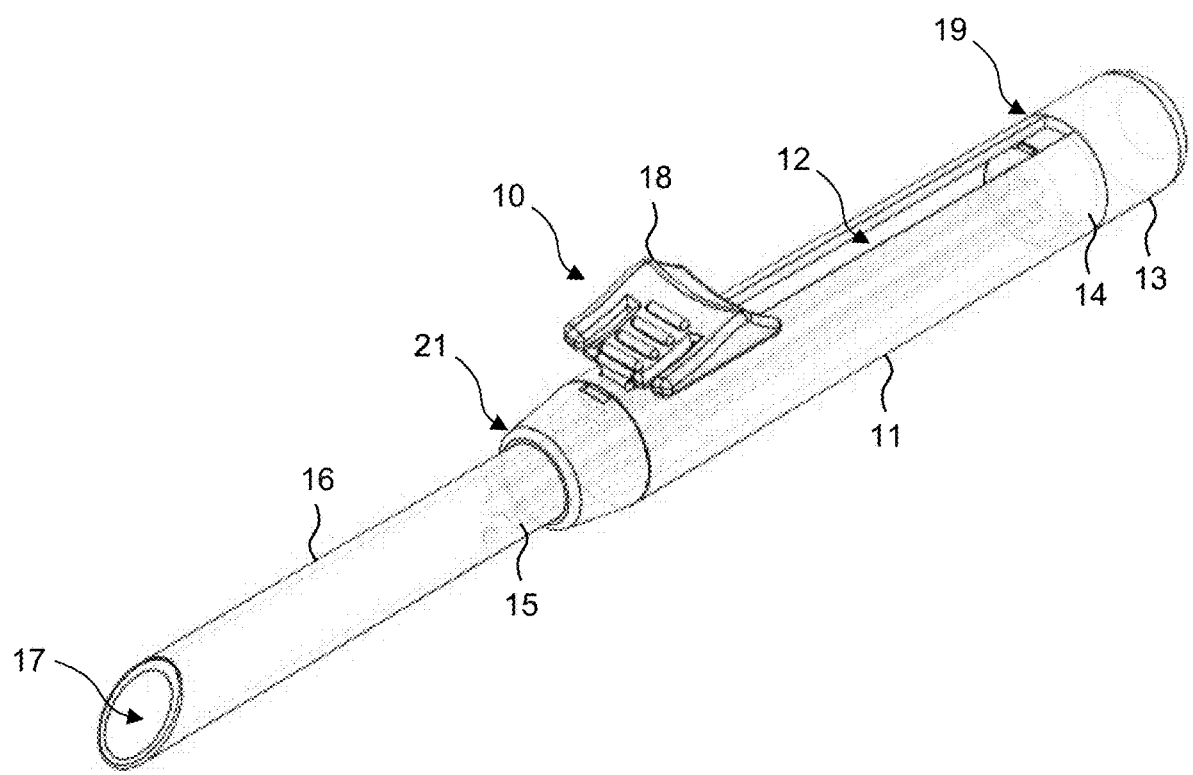
FIG. 1 is a block diagram showing, by way of example, a perspective view of an insertable physiological monitor injector tool.

The minimally invasive incision tool can include an insertion tube, a handle, and an arbor. FIG. 1 is a block diagram showing, by way of example, a perspective view 10 of an insertable physiological monitor injector tool 10. The injector tool 10 can include a handle 11 with a recess formed in an interior of the handle, along a longitudinal axis. The handle 11 can have a cylindrical semi-circular or rectangular shape, as well as other types of shapes. In one embodiment, a shape of the handle can be based on a shape of an implantable physiological monitor (IPM) to be injected into a patient using the injection tool. A proximal end 19 of the handle can be enclosed, while a distal end 21 of the handle can be open to allow access to the recess.

An insertion tube 16, which can have a different shape or the same shape as the handle, is provided in the recess of the handle. The insertion tube 16 can have a hollow interior 17 and be sized to fit in the recess 12 of the handle. At a minimum, a length of the insertion tube 16 should extend just beyond a distal end 21 of the handle via the opening. A distal end of the insertion tube can include a beveled edge or a straight edge, and can be sharpened or unsharpened. In a further embodiment, a tip can be attached to the distal end of the injector tube, as further described below with respect to the FIGS. 12 and 13.

A button or tab 18 is affixed to the insertion tube 16 to allow a user to move the insertion tube 16 within the recess. The button or tab 18 is positioned over an outer surface of the handle 11 via a channel 22 formed by a cutout in the handle 11. The button can slide back and forth within the channel 22 to move the insertion tube 16 back and forth within the recess of the handle 11.

An arbor 15 fits within the insertion tube 16 and is affixed on one end to a proximal end 19 of the handle 11 or to a separate end piece 13 attached to the proximal end of the handle. In one embodiment, a proximal end of the arbor 15 is affixed to a support mount 14 that is then affixed to the proximal end of the handle or the separate end piece 13. The arbor 15 can be shaped as a circle, square, rectangle, oval, cross, or a different shape, and sized to fit within the insertion tube 16. A length of the arbor 15 can be dependent on a length of the handle and should extend slightly past the distal end of the handle 11. The arbor 15 remains in a fixed position, while the insertion tube 16 slides back and forth over the arbor 15.

Figure 2:
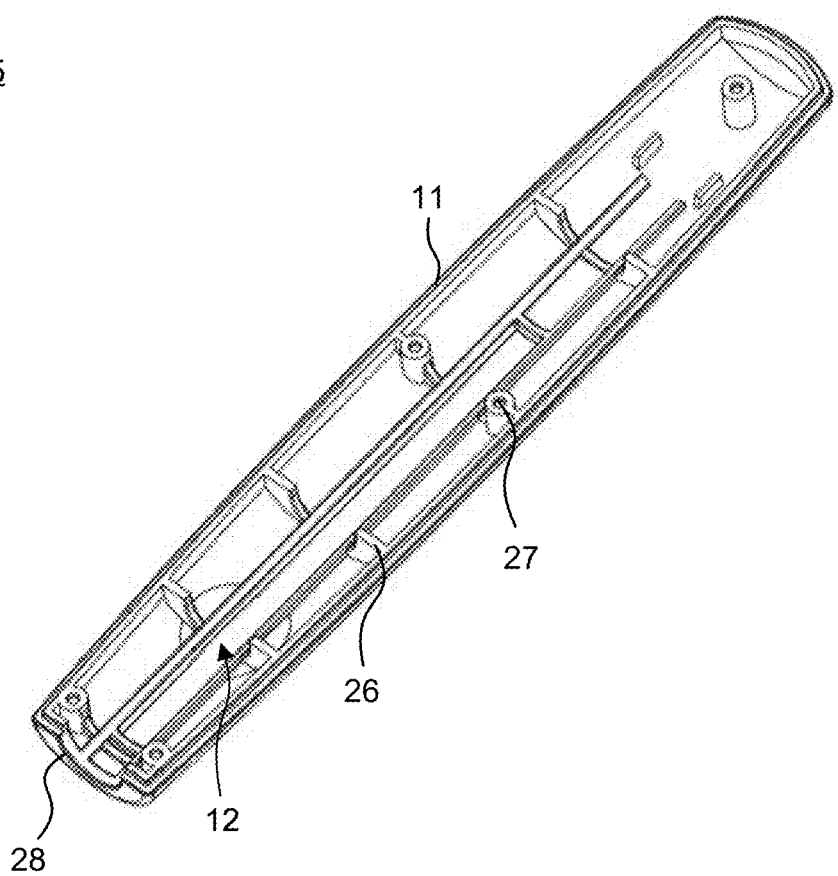
FIG. 2 is a block diagram showing, by way of example, an interior view of a cross section of a handle of the insertable physiological monitor injector tool of FIG. 1.

To ensure smooth movement of the insertion tube 16 within the handle 11, the handle can be conformed to fit securely around the insertion tube 16 with a slight space between an interior surface of the handle 11 and an exterior of the insertion tube 16. When the shape of the handle 11 differs from the insertion tube 16, an interior of the handle 11 can include guides to allow smooth movement of the insertion tube 16. FIG. 2 is a block diagram showing, by way of example, an interior view 25 of a cross section of a handle of the insertable physiological monitor injector tool of FIG. 1. The handle 11 can be formed from a single piece of material or from two or more pieces. The material can include plastic, metal, or stainless steel, as well as other types of material. In an interior of the handle 11, guides 26 can be formed along the recess 12 to guide the insertion tube (not shown) along the longitudinal axis of the recess 12. The guides can be formed as tabs of material, such as plastic, metal, or stainless steel, that extend from an interior surface of the handle 11. The guides can extend around or partially around the insertion tube (not shown). One or more sets of guides can be provided in the handle and each set can include two guides, which are each formed on either side of the insertion tube.

When the handle is formed from multiple pieces of material, screw holes or other fastening mechanism 27 can be formed along an interior of the handle. Screw holes or other fastening mechanism located on another piece of the handle should correspond with the screw holes on a first piece to secure the different pieces of the handle 11 together. At least one end of the handle is open 28, including the proximal end 21 of the handle to allow movement of the insertion tube (not shown) in and out of the handle 11.

Figure 3:
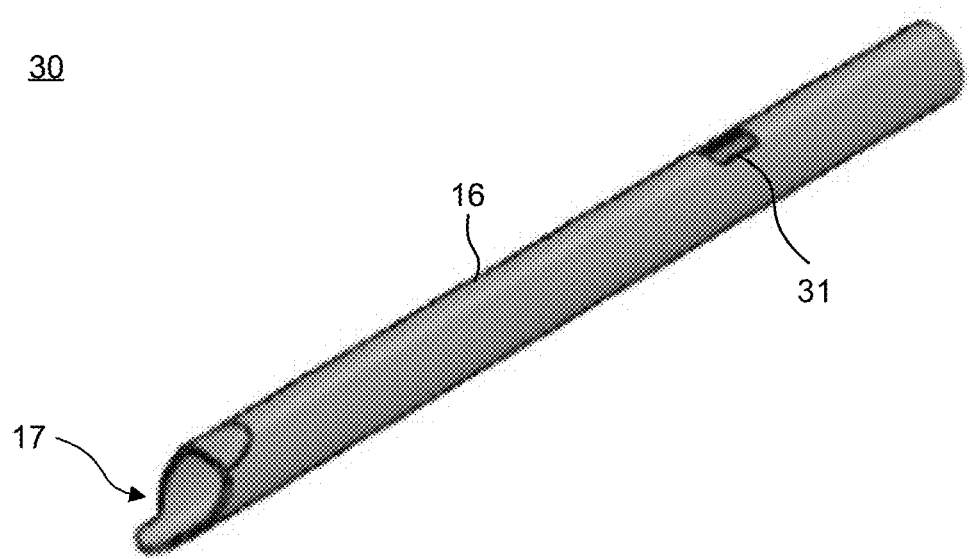
FIG. 3 is a block diagram showing, by way of example, a perspective view of an insertion tube of the insertable physiological monitor injector tool of FIG. 1.

The insertion tube slides within the recess via a button or tab. FIG. 3 is a block diagram showing, by way of example, a perspective view 30 of an insertion tube 16. The insertion tube 16 can be formed as a cylindrical tube with a hollow interior. However, other shapes are possible. Both ends of the insertion tube 16 can be open 17 to allow movement of the insertion tube 16 over the arbor (not shown). A cutout 31 is formed in a surface of the insertion tube 16 to affix to the button (not shown). For example, the button (not shown) can include a tab that is inserted into and secured in the cutout to allow a user to slide the button and thus, the insertion tube 16.

The insertion tube 16 can be made from material, including metal, stainless steel, plastic, or other types of material. When made from plastic, the IPM can be recharged while inserted in the insertable physiological monitor injector tool 10, as described below in further detail. A length of the insertion tube can be dependent on a location of an implantation site at which the IPM will be implanted. For example, an implantable cardiac monitor can be implanted between the skin and ribs of a wearer. Accordingly, the insertion tube 16 must be long enough to extend past the skin of a patient, but not longer than a distance between the ribs and the skin. Further, a shape of the insertion tube can be dependent on the IPM to be inserted in a wearer. For example, the insertion tube can be cylindrical when the IPM is cylindrical.

Figure 4:
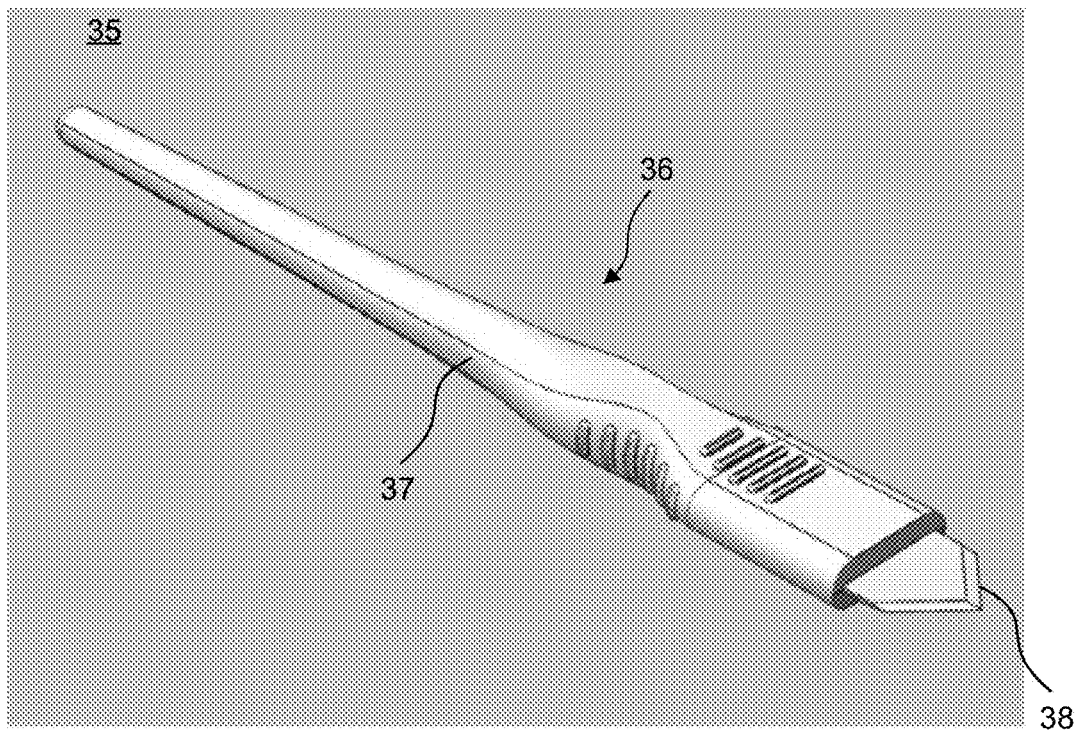
FIG. 4 is a block diagram showing, by way of example, a perspective view of an incision tool.

Implantation of the IPM can utilize an incision tool, tunneller tool, and the insertable physiological monitor injector tool. FIG. 4 is a block diagram showing, by way of example, a perspective view 35 of an incision tool 36. The incision tool 36 includes a handle 37 and a blade 38. The blade can be in the shape of a triangle, rectangle, or another shape. When shaped as a triangle, a base of the triangle can be affixed to a distal end of the handle 37 and an apex of the triangle facing outward from the handle 37. The incision tool 36 is used to make an incision in the skin of a patient after the incision area has been cleaned and sanitized.

Figure 5:
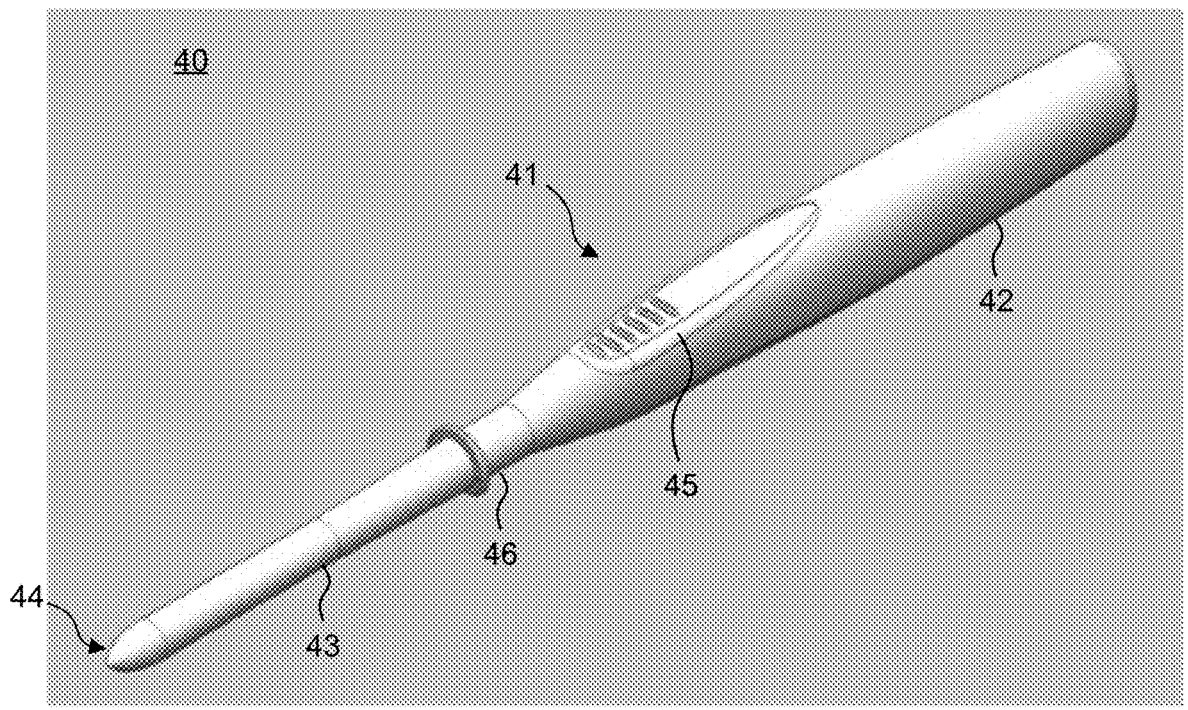
FIG. 5 is a block diagram showing, by way of example, a perspective view of a tunneller tool.

After an incision has been made, a tunneller tool is used to clear a path in the patient's tissue for later insertion of the insertable physiological monitor injector tool. FIG. 5 is a block diagram showing, by way of example, a perspective view 40 of a tunneller tool 41. The tunneller tool 41 includes a handle 42, a stopper or depth meter 46, and a rod 43. The handle 42 includes a grip 45 for a user when inserting the tunneller into a patient. The stopper or depth meter 46 is affixed on a distal end of the handle to provide a particular length of the rod which is to be inserted into the patient, while the rod 43 extends from the stopper. The stopper or depth meter 46 can be stationary or adjustable to adjust a length of the rod for different depth insertions in the patient. A distal end of the rod can include a tip 44 that can be sharpened or unsharpened. A length of the rod 43 can be dependent on a location of the IPM to be placed.

The tip 44 of the rod is inserted into the incision made by the incision tool. Once inserted, the user pushes the rod further into the patient via the handle 42 to clear a path in the tissue for placement of the IPM. The user can push the tunneller tool 41 into the patient until the stopper touches or is adjacent to the skin of the patient. Subsequently, the user removes the tunneller tool 41 from the patient.

Figure 6:
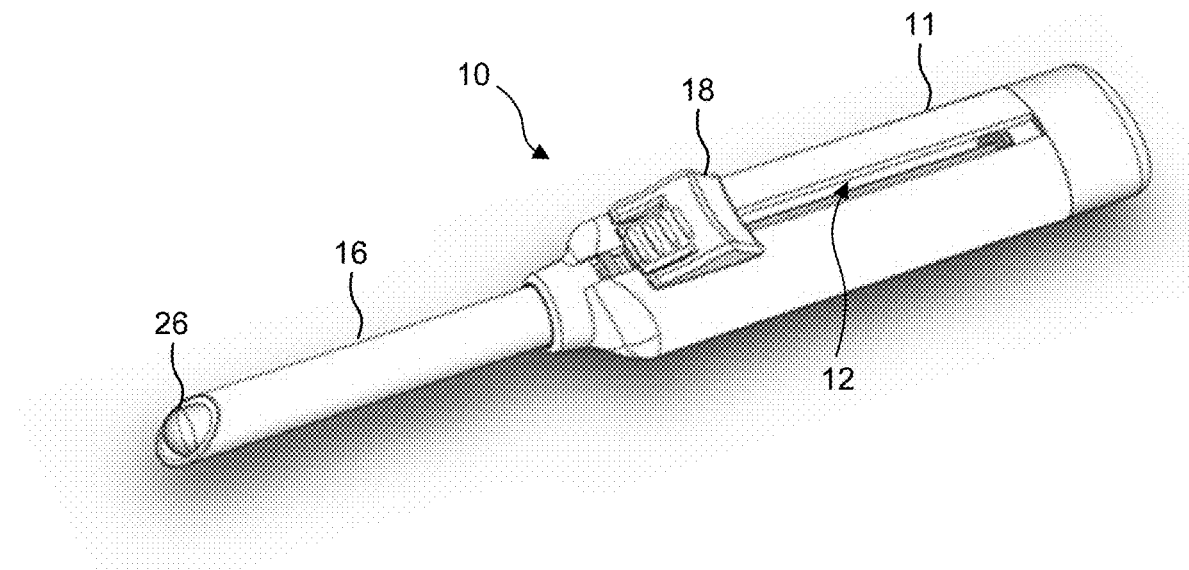
FIG. 6 is block diagram showing, by way of example, a perspective view of an insertable physiological monitor injector tool loaded with an insertable physiological monitor.

Once the incision has been made and a path is cleared for placement of the IPM, the insertable physiological monitor injector tool can be inserted into the patient. FIG. 6 is block diagram showing, by way of example, a perspective view 45 of an insertable physiological monitor injector tool loaded with an IPM. For injection, the insertion tube 16 can be in an extended position, outside of the recess of the handle 11. An ICM 26 is placed within the insertion tube 16 and is adjacent on a proximal end to the arbor (not shown).

A distal end of the extended insertion tube 16 is inserted into the incision on the patient and a user moves the insertable physiological monitor injector tool into the tissue of the patient using the path formed by the tunneller tool. In one embodiment, the user can press down on or distally against the button 18 to prevent the insertion tube 16 from retracting towards a proximal end of the handle 11 via the recess 12. However, in a further embodiment, the button can be in a locked position to prevent retraction of the insertion tube 16.

Figure 7:
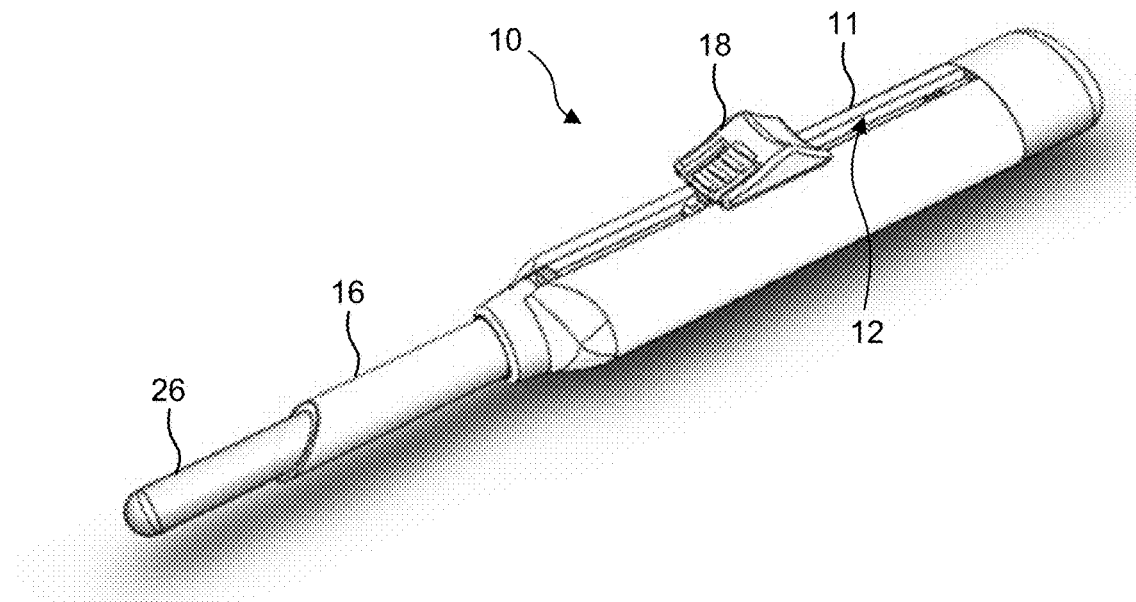
FIG. 7 is a block diagram showing, by way of example, a perspective view of an insertable physiological monitor injector tool in a partially retracted position.

Once a desired location has been reached by the distal end of the insertion tube 16, FIG. 7 is a block diagram showing, by way of example, a perspective view 50 of an insertable physiological monitor injector tool 10 in a partially retracted position. The insertable physiological monitor injector tool 10 can be inserted into the patient until the distal end of the housing touches or is adjunct to an outward facing surface of the patient's skin. Once reached, the button 18 can be pressed or released from a spring loaded or locked position, depending on a type of safety mechanism, and slowly moved along the channel 12, towards the proximal end of the handle 11. As the button is moved proximally, the insertion tube 16 slides over the IPM 26 which is stationary and begins to get exposed to the patient's tissue as the insertion tube retracts.

Figure 8:
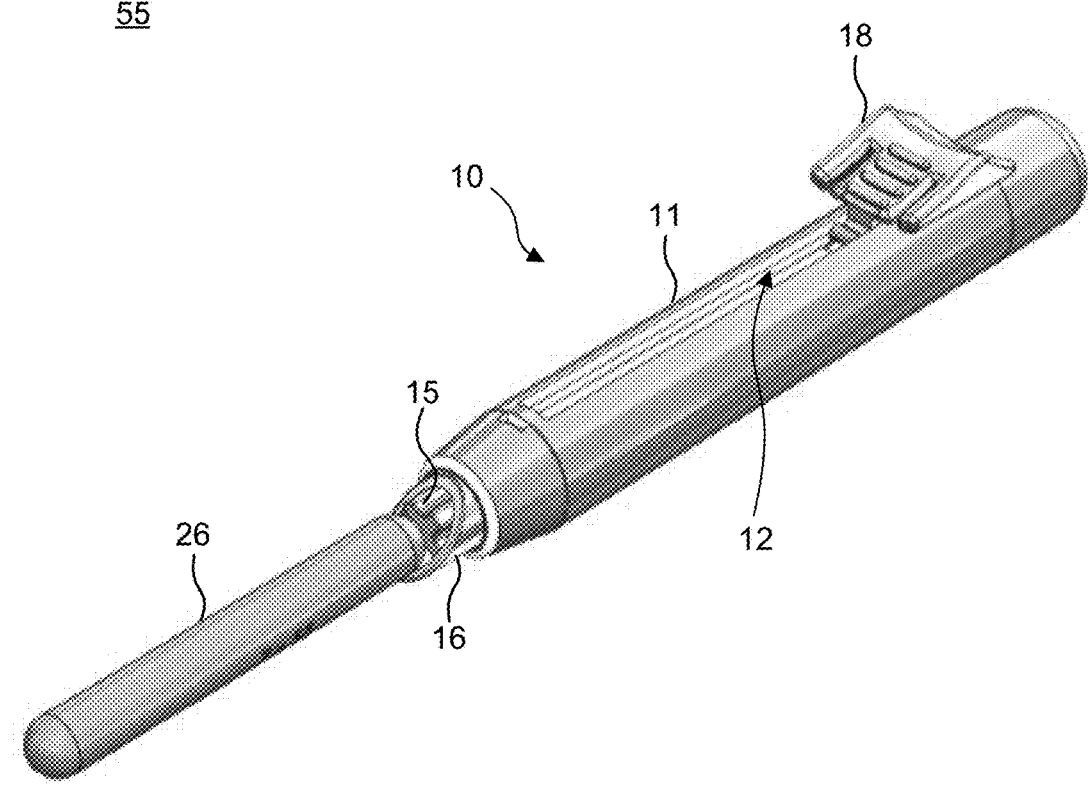
FIG. 8 is a block diagram showing, by way of example, a perspective view of an insertable physiological monitor injector tool in a fully retracted position.

Once the insertion tube has been fully retracted, the IPM is positioned outside of the insertion tube and fully in the tissue of the patient. FIG. 8 is a block diagram showing, by way of example, a perspective view 55 of an insertable physiological monitor injector tool 10 in a fully retracted position. To obtain the retracted position, the user should slide the button 18 the length of the channel 22, formed in the handle 11, to move the insertion tube 16 along the recess 12 into an interior of the handle 11. As the insertion tube is retracted, more of the IPM 26 is revealed and introduced to the tissue of the patient. The stationary arbor 15 within the insertable tube is adjacent to a proximal end of the IPM 26 and prevents the IPM 26 from retracting with the insertable tube 16. Thus, the IPM 26 remains in the patient's tissue and the insertable physiological monitor injector tool 10 is moved away from the patient after the insertion tube 16 has been fully retracted.

Figure 9:
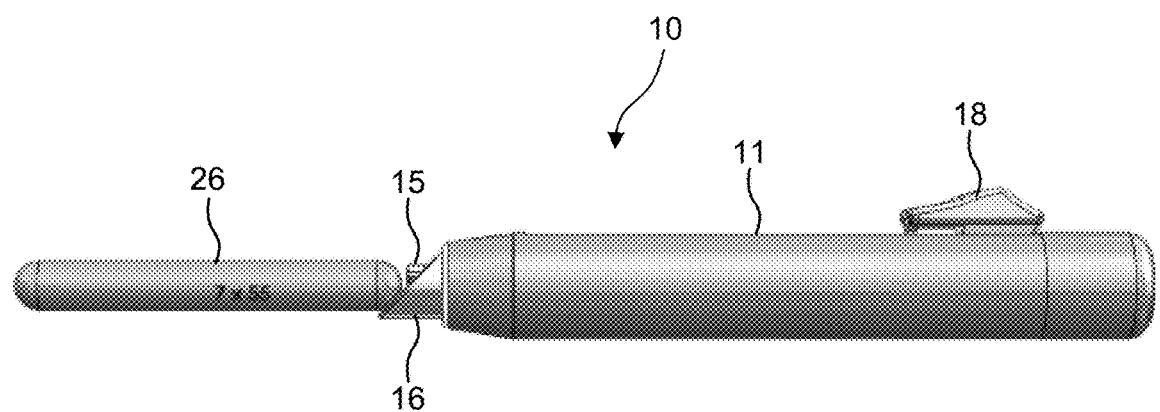
FIG. 9 is a block diagram showing, by way of example, a side view of an insertable physiological monitor injector tool in a fully retracted position.

FIG. 9 is a block diagram showing, by way of example, a side view 60 of an insertable physiological monitor injector 10 in a fully retracted position. In the fully retracted position, the button 18 is at the proximal end of the handle 11, the insertion tube 16 is fully retracted and a portion of the insertion tube 16 may extend slightly past the distal end of the handle. The arbor remains stationary and also extends slightly past the distal end of the handle, while the IPM 26 is no longer housed by the insertion tube 16 and is left in the tissue of the patient at the desired implantation site.

Figure 10:
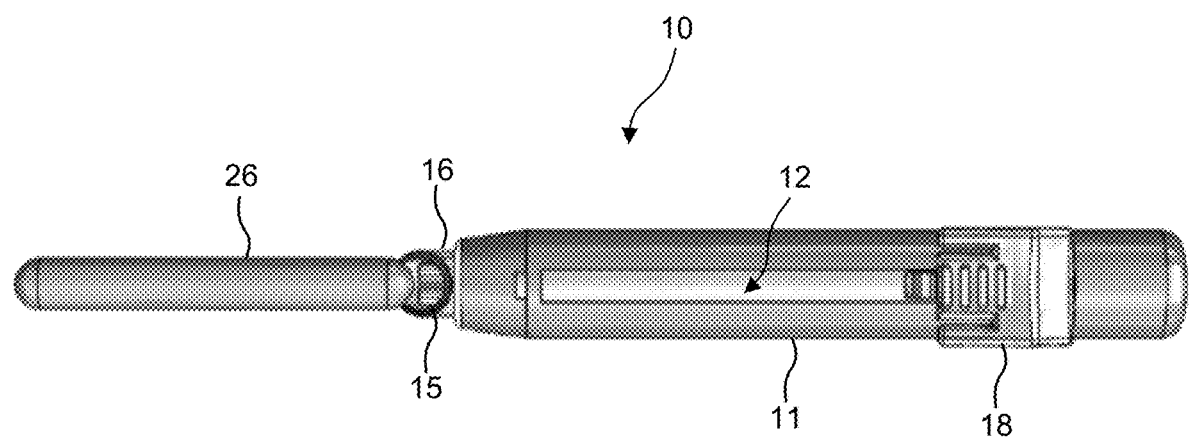
FIG. 10 is a block diagram showing, by way of example, a top view of an insertable physiological monitor injector tool in a fully retracted position.

FIG. 10 is a block diagram showing, by way of example, a top view 65 of an insertable physiological monitor injector tool 10 in a fully retracted position. When the insertion tube 16 is fully retracted, the button 18 is on a proximal end of the handle and the IPM 26 is no longer in the insertable physiological monitor injector tool 10. The IPM 26 is positioned in the tissue of the patient and remains as the insertable physiological monitor injector tool is removed from the patient. The arbor 15 prevents the IPM 26 from retracting with the insertion tube 16 along the recess of the handle during retraction and removal of the insertable physiological monitor injector tool 10.

Figure 11:
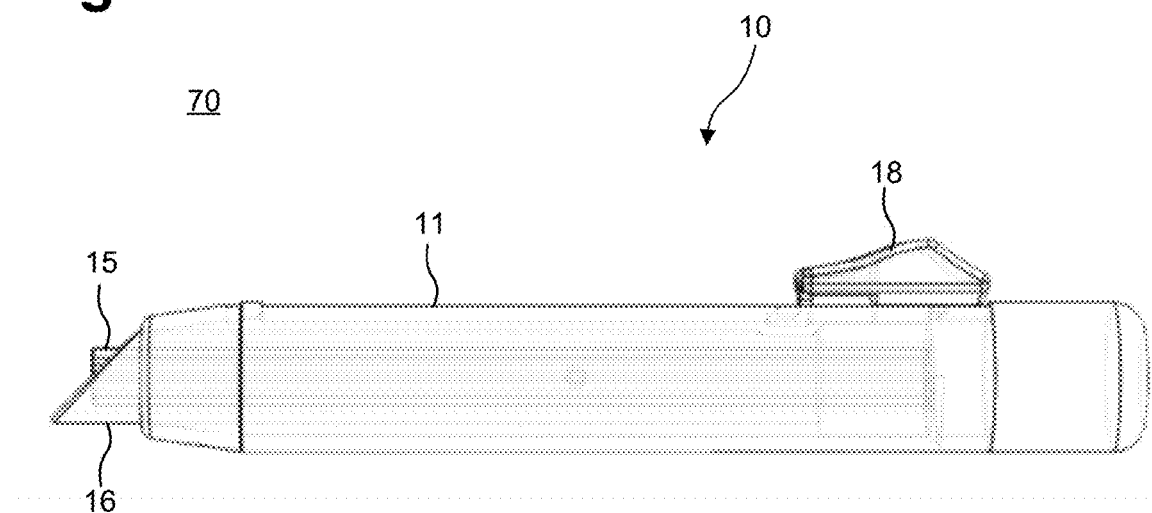
FIG. 11 is a block diagram showing, by way of example, a side view of an insertable physiological monitor injector tool in a fully retracted position.
Figure 12:
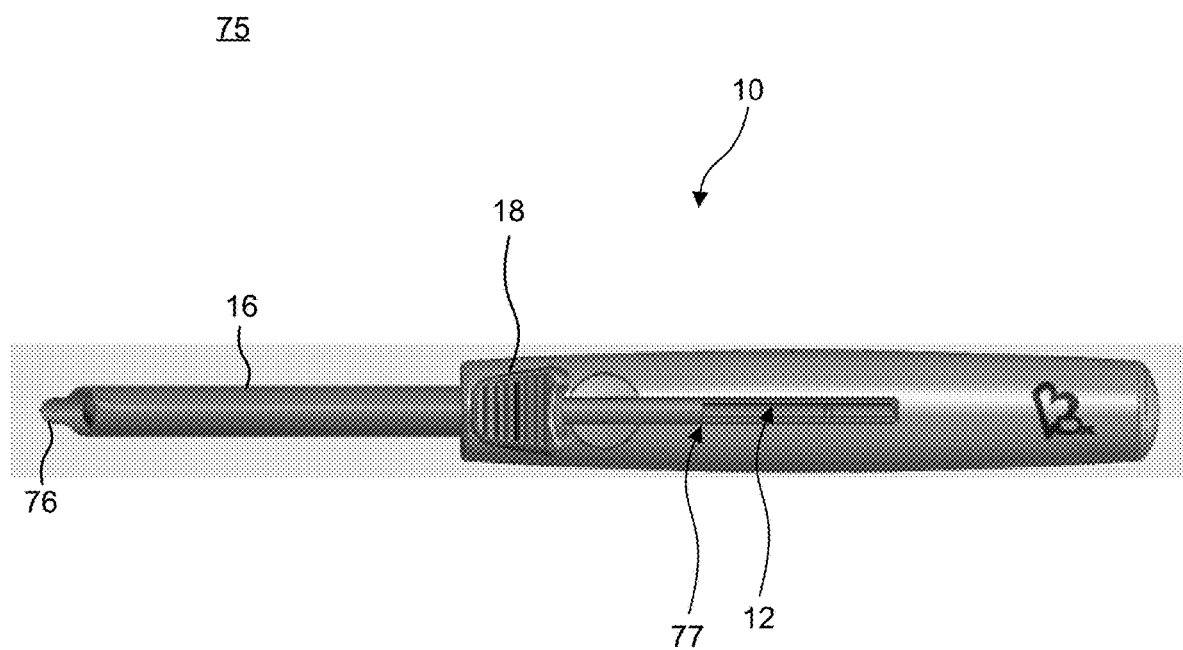
FIG. 12 is a block diagram showing, by way of example, a top view of a different embodiment of the insertable physiological monitor injector tool of FIG. 1.
Figure 13:
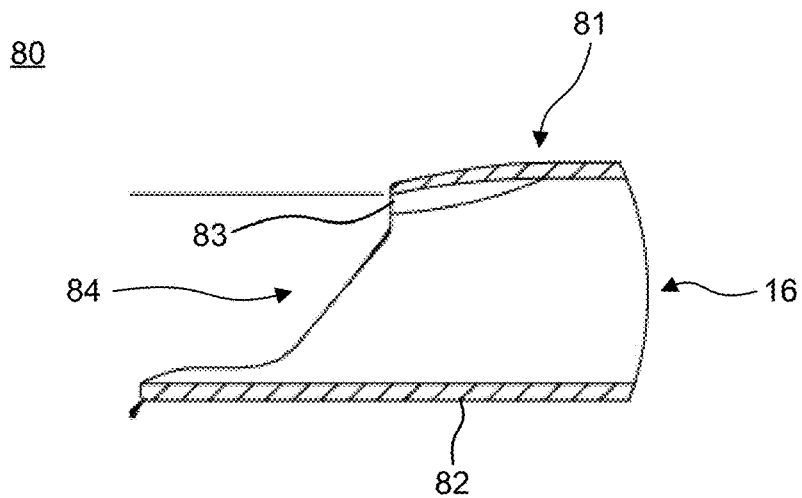
FIG. 13 is a block diagram showing, by way of example, a side view of a distal end of an insertion tube of the embodiment of the insertable physiological monitor injector of FIG. 12.

When in the fully retracted position, the arbor is positioned within the insertion tube and the insertion tube is within the recess of the handle. FIG. 11 is a block diagram showing, by way of example, a side view 70 of an insertable physiological monitor injector tool 10 in a fully retracted position. In the fully retracted position, the button 18 is on the proximal end of the insertable physiological monitor injector tool 10. The insertion tube 16 is positioned in the recess of the handle and the arbor 15 is positioned within the insertion tube 16. The above description of the insertable physiological monitor injector tool can have different embodiments. For example, FIG. 12 is a block diagram showing, by way of example, a top view 75 of a different embodiment of the insertable physiological monitor injector 10 of FIG. 1. A tip 76 can be formed on at least a portion of the distal end of the insertion tube 16. The tip 76 can be heat formed to prevent the IPM (not shown) from falling out of the insertion tube 16 during insertion into the patient. FIG. 13 is a block diagram showing, by way of example, a side view 80 of a distal end of an insertion tube16 of the embodiment of the insertable physiological monitor injector of FIG. 12. A distal end 81 of the insertion tube 16 can include a tip 83 for preventing an IPM placed in an interior 84 of the insertion tube 16 from falling out, especially when the injector tool is angled for insertion into a patient.

In one embodiment, the tip 81 can be formed on an upper surface of the insertion tube, nearest to the button. The tip 81 can be formed inward, into the hollow interior 84, to produce interference between the insertion tube and the ICM. For example, the material 82 of the insertion tube 16 can bend downward on the distal tip, into the hollow interior 84. However, bending the tip 83 too far into an interior of the insertion tube can prevent release of the IPM when the insertion tube retracts. Accordingly, the tip 83 should be formed to prevent the IPM from falling out, but allow the insertion tube to retract over the IPM, which is stationary due to the arbor (not shown).

In a further embodiment, the tip can include an additional piece of material affixed to an upper interior surface of the insertion tube material 82. The additional material can extend downward into the hollow interior of the insertion tube to prevent the IPM from falling out.

When the insertion tube 16 is fully extended, the button 18 is on a distal end of the handle 11 and the recess 12 in the handle 11 can be visible. Also, a proximal end 77 of the insertion tube 16 can be visible through the channel. However, when in a fully retracted position, the recess 12 may not be visible since the outer surface of the insertion tube 16 can block a view of the recess 12 via the channel 22.

Figure 14:
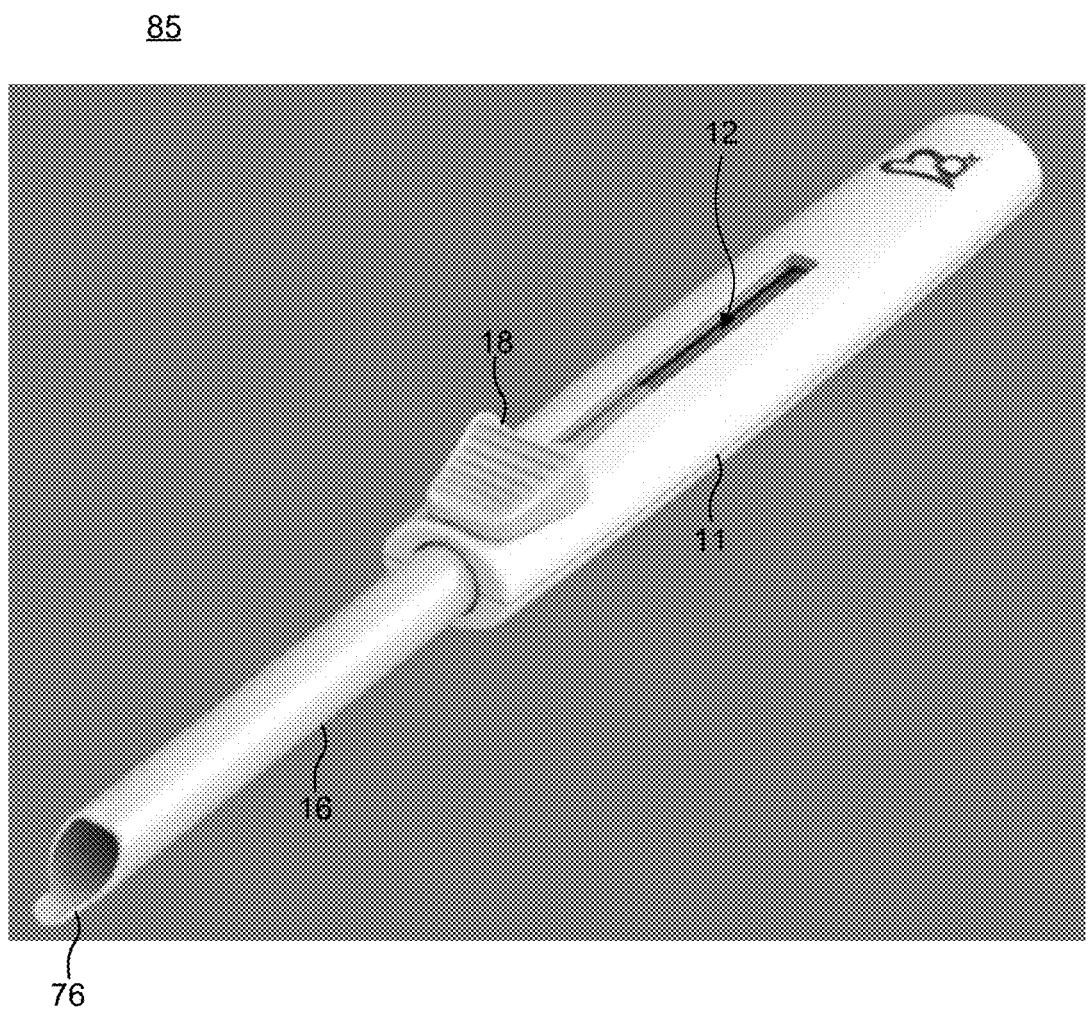
FIG. 14 is a block diagram showing, by way of example, a perspective view of the insertable physiological monitor injector tool of FIG. 8.

FIG. 14 is a block diagram showing, by way of example, a perspective view of the insertable physiological monitor injector of FIG. 12. In an extended position, the insertion tube 16 extends outward from the handle 11 and the button 18 is located on a distal end of the handle 11. The tip 76 extends from a distal end of the insertion tube 16 on a bottom surface of the opening. However, in a further embodiment, the tip can extend from a top surface or fully around the opening of the insertion tube 16 on the distal end. The tip can prevent the IPM (not shown) from moving outside of the insertion tube 16 when the insertable physiological monitor injector tool 10 is inserted into a patient.

Figure 15A:
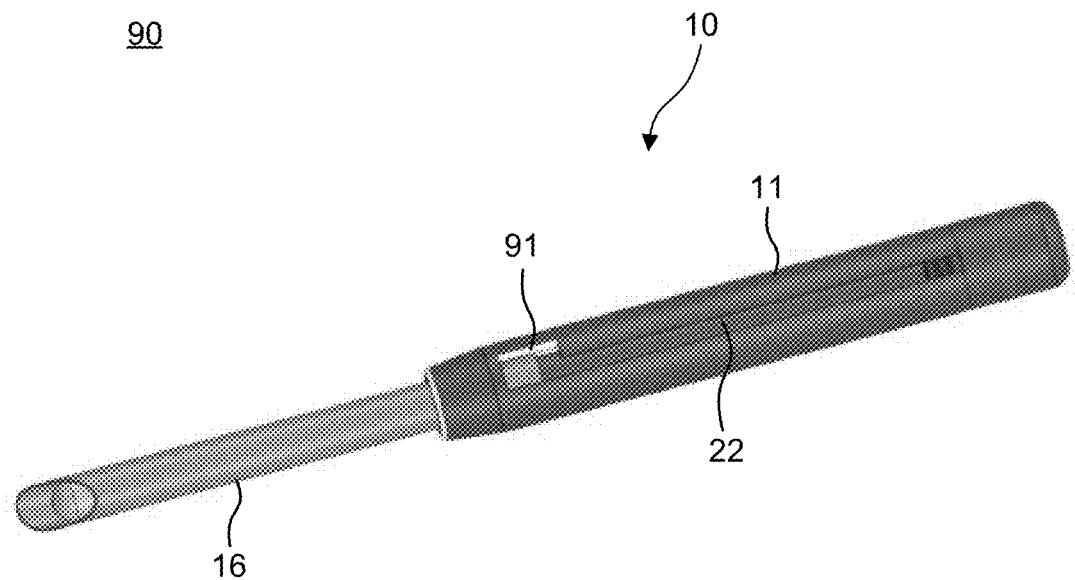
FIG. 15A is a block diagram showing, by way of example, a perspective view of an insertable physiological monitor injector tool with a channel.

FIGS. 15A-E are block diagrams showing, by way of example, a different embodiment of the insertable physiological monitor injector of FIG. 1. FIG. 15A is a block diagram showing, by way of example, a perspective view 90 of an insertable physiological monitor injector tool 10 with a channel 22. The housing 11 of the insertable physiological monitor injector tool 10 has a channel 22 formed within a surface, such as a top surface. The channel 22 can run along a longitudinal axis of the housing 11 and include a stem 91, which is formed on a distal end of the housing and extends outwards, away from the channel along the longitudinal axis. The stem 91 can function to lock the insertion tube 16 in an extended position via a tab (not shown).

Figure 15B:
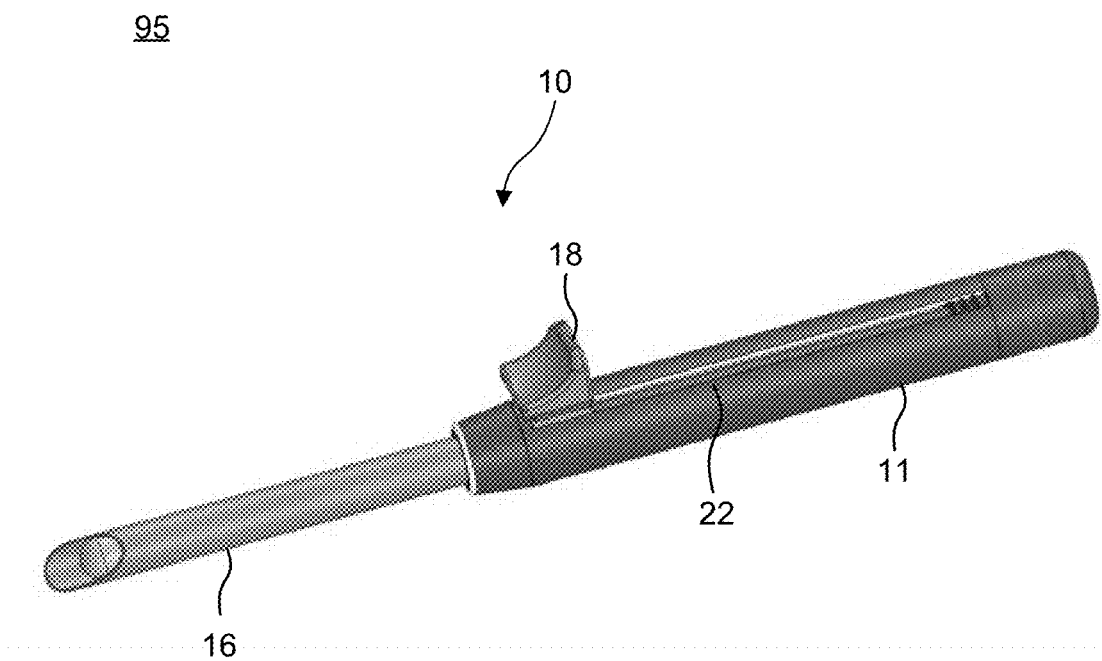
FIG. 15B is a block diagram showing, by way of example, a perspective view of an insertable physiological monitor injector tool with a tab in a channel stem.

FIG. 15B is a block diagram showing, by way of example, a perspective view 95 of an insertable physiological monitor injector tool 10 with a tab 18 in a channel stem. A tab, such as a button 18 can be in a locked position when located in the stem (not shown) of the channel 22 formed in the handle 11. Specifically, when in the stem, the button 18 is prevented from moving distally or proximally along the handle, which prevents movement of the insertion tube 16. Thus, when the button or tab 18 is locked, the insertion tube 16 is locked in an extended position.

Figure 15C:
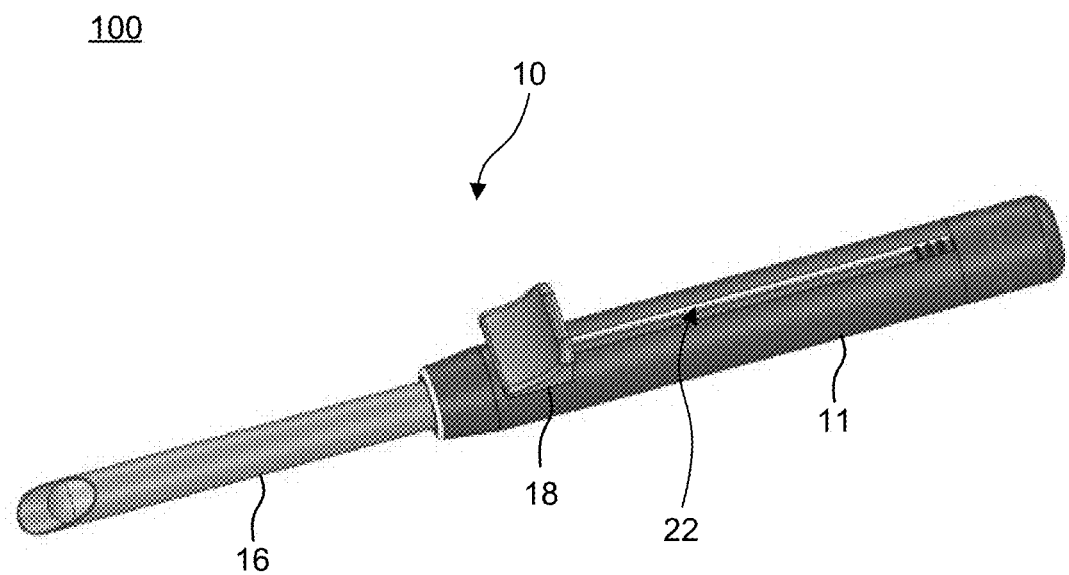
FIG. 15C is a block diagram showing, by way of example, a perspective view of an insertable physiological monitor injector tool with a tab on a distal end of a channel.

FIG. 15C is a block diagram showing, by way of example, a perspective view 100 of an insertable physiological monitor injector tool 10 with a tab 18 on a distal end of a channel 22. To unlock the insertion tube 16, of the insertable physiological monitor injector tool 10, from an extended position, a user slides a tab, such as a button 18 out of the stem (not shown) and into the channel 22. Specifically, a user moves the button or tab 18 across the longitudinal axis of the handle 11 and towards the channel 22.

Figure 15D:
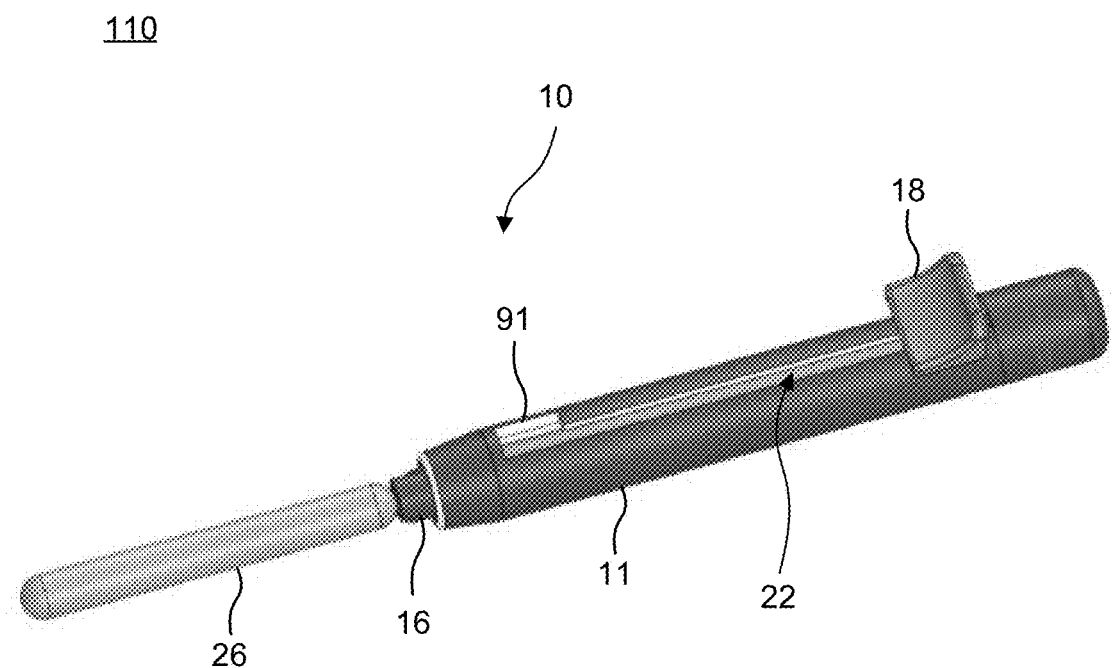
FIG. 15D is a block diagram showing, by way of example, a perspective view of an insertable physiological monitor injector tool with a tab on a proximal end of a channel.

FIG. 15D is a block diagram showing, by way of example, a perspective view 110 of an insertable physiological monitor injector tool 10 with a tab 18 on a proximal end of a channel 22. To retract the insertion tube 16, a user slides the tab, such as a button 18, away from the channel stem 91, towards a proximal end of the handle 11, along the channel 22. When the button 18 is on the proximal end, the insertion tube 16 moves into the recess of the handle and totally clears or mostly clears the IPM 26, leaving the IPM implanted in the tissue of a patient.

Figure 15E:
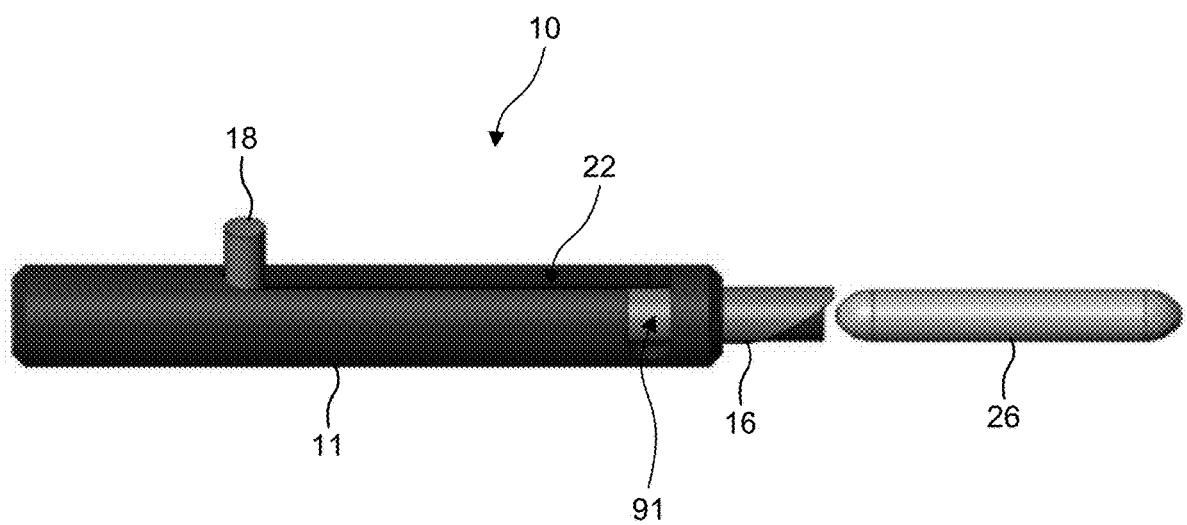
FIG. 15E is a block diagram showing, by way of example, a side view of an insertable physiological monitor injector tool with a tab.

FIG. 15E is a block diagram showing, by way of example, a side view 120 of an insertable physiological monitor injector tool 10 with a tab 18. The tab can include a button, knob, pin, or other type of device that is capable of attachment to the insertion tube 16 and movement by the user. At a minimum the tab should be movable from a locked position in a channel stem 91, into a channel 22, and then along the channel 22. As the tab 18 is moved proximally along the channel 22, the insertion tube retracts into an interior of the housing 11, leaving the IPM 26 in the tissue of a patient.

In one embodiment, the IPM can be packaged with the insertable physiological monitor injector tool, such as by placing the IPM in the insertion tube. The injection tube is in the extended position to provide room in which the IPM can be placed on a distal end of the arbor, a portion of which is also inside the insertion tube in the extended position. Based on how much time passes from packaging of the IPM with the injector tool to injection of the IPM in a patient, battery power of the IPM may run low. Ideally, the IPM should be fully charged prior to insertion into the patient to ensure that all functions of the IPM are working. When the insertion tube is made from a conductive material that allows electromagnetic waves or energy to pass, the battery of the IPM can be recharged while remaining in the insertable physiological monitor injector tool, prior to placement in the patient. The material of the insertion tube can include plastic, metal or other types of material.

In one embodiment, the battery can be inductively charged via a wireless device that is placed over sterile packaging of the insertable physiological monitor injector tool. The wireless charging device can include a puck or wand or other type of device capable of wireless charging. The device wirelessly charges the battery until the battery is full. Subsequently, the insertable physiological monitor injector tool is removed from the package and used to insert the IPM in a patient.

The insertable physiological monitor injector tool can be constructed by building an elongated handle with a recess formed along a longitudinal axis in an interior of the handle. An insertion tube having a hollow elongated shape can be positioned within the recess of the elongated handle. One or more sets of guides are formed on an interior surface of the handle to surround and guide at least a portion of the insertion tube in the recess. In one embodiment, a notch can be formed on a proximal end of the insertion tube, which is moveable within the recess. A stationary arbor is placed within the insertion tube and affixed to a proximal end of the elongated handle, in the interior. When the insertion tube is in a retracted position, the stationary arbor extends through the insertion tube. A tab, such as a button or knob is affixed to the insertion tube via the notch. The tab can be used to lock the insertion tube in an extended position. An implantable physiological monitor is placed within the insertion tube when the insertion tube is in the extended position. A channel is formed within a portion of the handle, on the proximal end, to allow movement of the button to retract the insertion tube from the extended position to a retracted position.

While the invention has been particularly shown and described as referenced to the embodiments thereof, those skilled in the art will understand that the foregoing and other changes in form and detail may be made therein without departing from the spirit and scope.

What is claimed is:

1. An insertable physiological monitor injector tool, comprising:
   a cylindrical handle within which a recess is formed along a longitudinal axis and comprising an opening on a distal end, wherein a hollow structure is housed in the recess;
   a stationary arbor affixed to a proximal end of the cylindrical handle, wherein the stationary arbor is configured to extend past the distal end of the cylindrical handle, and wherein the stationary arbor is configured to extend past a distal end of the hollow structure when the hollow structure is in a fully retracted position; and
   an implantable cardiac monitor, wherein the implantable cardiac monitor is inductively chargeable while preloaded in the hollow structure of the insertable physiological monitor injector tool,
   wherein the hollow structure of the insertable physiological monitor injector tool is comprised of plastic and configured to inject the implantable cardiac monitor preloaded in the hollow structure into a chest of a patient, and
   wherein the hollow structure includes a beveled end, wherein the beveled end bends inwards into the hollow structure and is configured to secure the implantable cardiac monitor within the hollow structure prior to implantation but allow the hollow structure to retract over the implantable cardiac monitor during implantation, and at least a portion of the beveled end is inserted into the chest of the patient during implantation of the implantable cardiac monitor.

2. The insertable physiological monitor injector tool according to claim 1, wherein the hollow structure comprises an insertion tube having a hollow elongated shape.

3. The insertable physiological monitor injector tool according to claim 2, further comprising a tab affixed to the insertion tube, wherein the tab is configured to lock the insertion tube in an extended position.

4. An insertable physiological monitor injector tool, comprising:
   a cylindrical handle within which a recess is formed along a longitudinal axis and comprising an opening on a distal end;
   a hollow elongated tube that is movably positioned within the cylindrical handle, in the recess, and comprising a cutout formed in a surface on one end of the hollow elongated tube in a shape of a square or rectangle and a beveled end opposite the end with the cutout, wherein the beveled end bends inwards into the hollow elongated tube and is configured to secure an implantable physiological monitor within the hollow elongated tube prior to implantation but allow the hollow elongated tube to retract over the implantable physiological monitor during implantation,
   wherein the implantable physiological monitor is inductively chargeable while preloaded in the hollow elongated tube;
   a stationary arbor affixed to a proximal end of the cylindrical handle, wherein the stationary arbor is configured to extend past a distal end of the cylindrical handle, and wherein the stationary arbor is configured to extend past a distal end of the hollow elongated tube when the hollow elongated tube is in a fully retracted position; and
   a tab affixed directly to the hollow elongated tube via the cutout formed in the surface of the hollow elongated tube, wherein a bottom of the tab is secured into the cutout and a top of the tab extends outside the cylindrical handle, and the tab is configured to lock the hollow elongated tube in an extended position.

5. The insertable physiological monitor injector tool according to claim 4, wherein the hollow elongated tube is configured to accept the implantable physiological monitor when the hollow elongated tube is in the extended position.

6. The insertable physiological monitor injector tool according to claim 4, wherein a channel is formed within a portion of the cylindrical handle, on the proximal end, to allow movement of the tab.

7. The insertable physiological monitor injector tool according to claim 6, wherein the hollow elongated tube is configured to retract into the cylindrical handle via the recess upon movement of the tab in the channel towards a proximal end of the cylindrical handle.

8. The insertable physiological monitor injector tool according to claim 4, wherein the hollow elongated tube is made from plastic.

9. The insertable physiological monitor injector tool according to claim 4, wherein a distal end of the hollow elongated tube is sharpened.

10. The insertable physiological monitor injector tool according to claim 4, further comprising:
    one or more sets of guides formed on an interior surface of the recess and shaped to surround at least a portion of the hollow elongated tube in the recess.

11. The insertable physiological monitor injector tool according to claim 4, further comprising:
    a tip formed on a distal end of the hollow elongated tube.

12. An insertable physiological monitor injector tool system, comprising:
    a cylindrical handle within which a recess is formed along a longitudinal axis;
    a hollow elongated tube that is movably positioned within the cylindrical handle, in the recess, and comprising a cutout formed in a surface on one end of the hollow elongated tube in a shape of a square or rectangle and a beveled end opposite the end with the cutout, wherein the beveled end bends inwards into the hollow elongated tube and is configured to secure an implantable physiological monitor within the hollow elongated tube prior to implantation but allow the hollow elongated tube to retract over the implantable physiological monitor during implantation,
    wherein the implantable physiological monitor is inductively chargeable while preloaded in the hollow elongated tube;
    a stationary arbor affixed to a proximal end of the cylindrical handle, wherein the stationary arbor is configured to extend past a distal end of the cylindrical handle, and wherein the stationary arbor is configured to extend past a distal end of the hollow elongated tube when the hollow elongated tube is in a fully retracted position;
    a tab directly affixed to the hollow elongated tube via a cutout formed in a surface of the hollow elongated tube, wherein a bottom of the tab is secured into the cutout and a top of the tab extends outside the cylindrical handle, and the tab is configured to lock the hollow elongated tube in an extended position; and
    a charging device to recharge a battery of the insertable physiological monitor.

13. The system according to claim 12, further comprising:
    an incision tool comprising a handle and a blade affixed to a distal end of the handle.

14. The system according to claim 12, further comprising:
    a tunneller tool comprising a handle and a rod affixed to a distal end of the handle.

15. The system according to claim 12, wherein the hollow elongated tube is plastic.

16. The system according to claim 12, further comprising:
    a tip formed on a distal end of the hollow elongated tube.

* * * * *